United States Patent [19]

Nuzzolo et al.

[11] Patent Number: 5,210,018
[45] Date of Patent: May 11, 1993

[54] IMMUNOENZYMATIC METHOD IN HOMOGENEOUS PHASE FOR THE DETERMINATION OF ANTI-PLASMODIUM FALCIPARUM-SPOROZOITE ANTIBODIES IN HUMAN BLOOD

[75] Inventors: Carlo A. Nuzzolo, Rome; Adriano Bernardi, Monterotondo; Antonello Pessi, Rome; Antonio S. Verdini, Monterotondo, all of Italy

[73] Assignee: Eniricerche S.p.A., Milan, Italy

[21] Appl. No.: 341,041

[22] Filed: Apr. 20, 1989

[30] Foreign Application Priority Data

May 13, 1988 [IT] Italy ................... 20561 A/88

[51] Int. Cl.$^5$ ................ G01N 33/539; G01N 33/569
[52] U.S. Cl. ................... 435/7.22; 435/7.9; 435/947; 435/975; 436/539
[58] Field of Search .............. 435/7.22, 7.9, 975, 435/947; 436/539

[56] References Cited

U.S. PATENT DOCUMENTS

| | | | |
|---|---|---|---|
| 4,843,146 | 6/1989 | Bernardi et al. | 435/7.22 |
| 4,855,242 | 8/1989 | Soeldner | 436/539 |
| 4,977,079 | 12/1990 | Nuzzolo et al. | 435/7.22 |

FOREIGN PATENT DOCUMENTS 8304102 11/1983 World Int. Prop. O. .

OTHER PUBLICATIONS

G. Del Giudice et al, Journal of Clinical Micobiology, vol. 25, Jan. 1987, pp. 91-96.
F. Zavala et al, Journal of Immunological Methods, vol. 93, No. 1, Oct. 23, 1986, pp. 55-61.
Worthington Enzyme Manual, Worthington Biochemical Corporation, Freehold, N.J., 1972, pp. 43-45.

*Primary Examiner*—David Saunders
*Attorney, Agent, or Firm*—Shea & Gould

[57] ABSTRACT

An immunoenzymatic method for the detection of anti-*Plasmodium falciparum*-sporozoite antibodies in a sample of human blood, which operates, in homogeneous phase, and under suitable conditions, with a synthetic polypeptidic antigen (P), a synthetic antigen-enzyme (P-E) conjugate, wherein said antigen is capable of specifically reacting with the anti-*Plasmodium falciparum*-sporozoite antibodies (Ab) possibly present in the sample, and an inert substance capable of quantitatively precipitating the antibody-synthetic antigen-enzyme complex (Ab-P-E).

The method, due to its specificity, sensitivity, reproducibility and rapidity, is particularly useful in the epidemiological investigations into malaria and in the evaluation of the efficacy of an antimalarial vaccine.

10 Claims, No Drawings

IMMUNOENZYMATIC METHOD IN HOMOGENEOUS PHASE FOR THE DETERMINATION OF ANTI-PLASMODIUM FALCIPARUM-SPOROZOITE ANTIBODIES IN HUMAN BLOOD

The present invention relates to a novel immunoenzymatic method for the diagnosis of infection by malarial parasites in man.

More particularly, the present invention relates to an immunoenzymatic method for the detection in homogeneous phase of antibodies against *Plasmodium falciparum* sporozoites.

Malaria, one among the most serious parasitical infections in man, is caused by a protozoan belonging to Plasmodium genus, which develops, according to a multi-step cycle, partially inside the vertebrated host (man), and partially inside the carrier, the mosquito.

The infection arises in man with the inoculation by the anopheles mosquito of the sporozoitic form of Plasmodium.

The main species of Plasmodium which cause malaria in man are:
*Plasmodium ovale, Plasmodium malariae, Plasmodium vivax* and *Plasmodium falciparum*.

This latter, in particular, represents not only the most diffused species, but also that species, which causes the occurrence of most cases of illness and mortality associated with said infection.

At present, malaria is in a step of great revival, above all in tropical regions of Asia, Africa and America, owing to the appearance and the uncontrolled diffusion of drug-resistant parasites and of the degradation of the control systems, with the consequent increase in costs of fight programmes.

A basic element in the management of an antimalarial campaign consists in obtaining information about the incidence of the infection before, during and at the end of said campaign.

This requires hence the availability of a diagnostic method suitable for large-scale studies, and simultaneously endowed with a high degree of sensitivity.

In the art, methods are known for the diagnosis of malaria in man, by means of the microscopic examination of blood, or by means of immunological methods essentially based on measurements of fluorescence (IFA) (Nardin, E. H. et al. (1979) Bull WHO 57 (Suppl. 1), 211–217) and of radioactivity (IRMA) [Zavala, F. et al. (1985) Science, 228, 1436].

Said known processes are anyway not very suitable for epidemiological investigations, in which hundreds of thousands of samples are examined, such poor suitability being due, above all, to the long execution times required.

Furthermore, the IFA and IRMA processes suffer from the drawbacks which derive from the use of not very stable, or highly harmful, substances, such as the fluorescent substances and the radio-active isotopes.

In the art diagnostic methods are known, which exclude the usage of such substances, and are essentially based on the use of enzymes which catalyse a colorimetric reaction (EIA).

Among such methods, the most widely used one for the determination of malaria in man is the ELISA assay (Enzyme Linked Immunosorbent Assay), such as described, e.g., by Zavala, F. et al. (1985) Fed. Proc. 44, 980; Del Guidice, G. et al. (1987) J. Clin. Microbiol. 25, 91–96).

More particularly, according to said known method, a natural or synthetic antigen is bound, by a covalent linkage, or by adsorption, onto a solid support, such as, eg., polystyrene, and, after blocking the residual binding sites of said support with a suitable protein, is incubated with the serum under examination.

The process is then continued by adding to the reaction mixture, in succession, an anti-human-immunoglobulin antibody bound to a detector enzyme; and a colorless substrate, specific for the enzyme, which, in case the serum is positive, yields a coloured product.

Said method known from the prior art, although making it possible to overcome the problems, which derive from IRMA and IFA techniques, is anyway not free from drawbacks which derive both from the long execution times (about 6 hours), and from the use of such reactants as anti-human-immunoglobulin-enzyme antibodies which can only be obtained by means of complex and expensive processes. Furthermore, said method, in the present state of the application, shows a limit of sensitivity of about 1 ng of Ab/serum $\mu$l, and therefore it does not make it possible to detect the positivity of many sera with a lower antibody content.

In fact, in said assay, the specific value, obtained from the difference in absorbance between two supports, is strongly dependent upon the uniformity and reproducibility of the same supports, and therefore of the absorption of the antigen and of the protein.

Owing to its lower sensitivity, the ELISA test can furthermore cause a certain number of "false negative samples", whilst possible differences between the supports (wells of plates for microtitration) corresponding to a same sample can generate "false positive samples".

The values of sensitivity appear to be strongly influenced in said test by the fact that the reaction of formation of the antisporozoite antibody-antigen complex with the second antibody labeled with the enzyme, and the end colorimetric development are carried out in heterogeneous phase.

Furthermore, such supports as, e.g., plates pretreated with the antigen and with the protein long before use cause problems of stability and storage.

U.S. Pat. No. 4,977,079 discloses a modified ELISA method for the determination of malaria in man, which uses a synthetic antigen-enzyme conjugate, wherein the antigen is capable of reacting and specifically binding the anti-*P. falciparum*-sporozoite antibodies, and a protein suitably linked to a solid support, wherein said protein is capable of binding the antisporozoite antibodies of the antibody-antigen-enzyme complex.

By operating according to the method as disclosed in said U.S. patent, the execution times are advantageously reduced, but the problems remain, which derive form working in heterogeneous phase.

The present invention aims therefore at developing a simple, reproducible, fast to be carried out, sensitive and economically advantageous method for detecting malaria in man.

This objective is achieved according to the present invention by providing an immunoenzymatic method which operates in homogeneous phase and under suitable conditions, by means of the use of a synthetic antigen (P), a synthetic antigen-enzyme conjugate (P-E), and a substance capable of quantitatively precipitating the antisporozoite antibody-synthetic antigen complexes wherein the synthetic antigen is in its free form (P), and in its labeled form (P-E).

Therefore, a purpose of the present invention is an immuno-enzymatic method for the determination in homogeneous phase of anti-*P. falciparum*-sporozoite antibodies in a sample of human blood.

A further purpose of the present invention is a diagnostic kit for detecting anti-*P. falciparum*-sporozoite antibodies in a human blood sample, comprising the necessary reactants for carrying out the method according to the present invention.

Further purposes of the present invention will be clear from the reading of the specification, and of the following examples.

In particular, the immunoenzymatic method according to the present invention comprises:

a) separately incubating two aliquots of a same sample of human blood with a synthetic antigen-enzyme conjugate (P-E), wherein said antigen is capable of reacting with the anti-*P. falciparum*-sporozoite antibodies possibly present in the sample under examination and the enzyme is capable of catalysing a colorimetric reaction, in phosphate buffer solution at a pH value comprised within the range of from 6.5 to 8.00, in the presence of a non-ionic and/or weak anionic detergent at a concentration not lower than 0.05% (weight/volume or volume/volume) (W/V or V/V), and at a temperature comprised within the range of from 15° C. to 35° C., with an aliquot of the sample being previously admixed with the same synthetic antigen not labeled with the enzyme at such a concentration as to completely inhibit the formation of the antisporozoite antibody-synthetic antigen- enzyme complex (Ab-P-E);

b) adding to the samples treated as reported in the (a) step, an inert substance capable of quantitatively precipitating the antisporozoite antibody-synthetic antigen-enzyme complex at an end concentration comprised within the range of from 13% to 17% (W/V);

c) separating the precipitate from the reaction mixtures obtained in the (b) step, either by filtration or by centrifugation;

d) repeatedly washing the precipitate with a buffer solution to which the inert substance is added, up to an end concentration comprised within the range of from 13% to 17% (W/V);

e) dissolving the so obtained precipitate in a buffer solution at a pH value comprised within the range of from 4.0 to 5.5, containing a non-ionic and/or weak anionic detergent at an end concentration not lower than 0.05% (W/V or V/V), in the presence, or not, of the precipitating inert substance, at an end concentration comprised within the range of from 3% to 5% (W/V);

f) adding to the so obtained solutions, hydrogen peroxide and a colourless enzymatic substrate, capable of generating, in case the sample under examination is positive, a coloured product, and finally determining the intensity of the colour by means of a spectrophotometric test method.

The (a) Step

In accordance with the method of the present invention, in the (a) step the sample of human blood to be analysed can be whole blood, serum or plasma.

In particular, when whole blood is used, the suspended matters are eliminated by centrifugation or filtration, at the end of the reaction with the antigens in free and in conjugated form, or in the preceding step, by operating on the blood samples diluted with the buffer solution.

Synthetic antigens suitable for the purposes of the present invention are sequential polypeptides capable of recognizing and specifically binding the anti-*P. falciparum*-sporozoite-antibodies.

In particular, said polypeptides can be defined by the aminoacidic sequence $(Asn-Ala-Asn-Pro)_n$, wherein:
- Asn = asparagine,
- Ala = alanine, and
- Pro = proline, and wherein n has a value comprised within the range of from 3 to 40.

Said polypeptide, which reproduces exactly the peptidic segment of the circumsporozoitic protein (CS) of *P. falciparum*, can be prepared by means of a polycondensation method of such a type as disclosed in U.S. patent application No. 850.135.

The presence in said polypeptide of only two end functional chemical groups, i.e., $-NH_2$ and $-COOH$, makes it particularly useful for the preparation of the conjugate according to the present invention, in that it makes it possible to form a stable covalent linkage between the polypeptide and the enzyme, without endangering the catalytic activity of the same enzyme.

The conjugation of said sequential polypeptide with the enzyme can be carried out by operating according to general techniques.

The conjugate is preferably prepared as reported in U.S. patent application No. 134.229.

Enzymes which catalyse a colorimetric reaction can be selected from the group consisting of the enzymes which are generally used in an immunoenzymatic assay.

Examples of such enzymes are: peroxidase, acidic phosphatase, alpha-galactosidase and beta-galactosidase.

In particular, and in order to better illustrate the present invention, without anyway wishing to limit it, the synthetic antigen $(Asn-Ala-Asn-Pro)_{20}((NANP)_{20})$ and the peroxidase enzyme are used.

In accordance with the method of the present invention, two aliquots of a same sample of blood, suitably diluted in a phosphate buffer solution (PBS) at a pH value of from 6.5 to 8.00 are separately admixed with the same phosphate buffer solution containing the synthetic antigen-enzyme conjugate (P-E) at a concentration comprised within the range of from 1.0 to 2.0 $\mu g/ml$.

In particular, the buffer solution contains a non-ionic and/or weak anionic detergent (D) at an end concentration not lower than 0.05% (weight/volume or volume/volume) (W/V or V/V), or mixtures of such detergents, with a mutual ratio of about 1.

Non-ionic and weak anionic detergents can be selected from among those known in the art, and generally used in diagnostics.

Examples of said detergents are, respectively, Tween-20, Triton X, saponine (non ionic detergents) and sodium cholate (Na-C), sodium deoxycholate (Na-Doc) or sodium lauroyl-sarcosine (Na-L-Sar) (weak anionic detergents).

Preferably, Triton X-100 is used, at a concentration of, or approximately of, 0.05%; or mixtures of Triton X-100 and sodium lauril-sarcosine are used, with a ratio of the components to each other of 1.

According to the present invention, one of the two aliquots of the sample is previously admixed with the unlabeled synthetic antigen (P) in a strong molar excess relatively to the P-E conjugate, so that the free antigen in competition with P-E can form with the antisporozoite antibodies (Ab) possibly present in the sample, an Ab-P complex, and completely inhibit the formation of Ab-P-E.

In accordance with the present invention, the present Applicant found that a molar ratio of P/P-E of 100/1 totally inhibits the formation of the above-said complex.

The so-obtained reaction mixtures are then incubated at a temperature comprised within the range of from 15° to 35° C., preferably of from 20° to 30° C., for a time period comprised within the range of from 15 to 30 minutes, and preferably of 20 minutes.

The (b) Step

In the (b) step of the present method in accordance with the present invention, the Ab-P and Ab-P-E complexes possibly formed in the (a) step are precipitated by adding to the mixtures an inert substance (neither reactive nor denaturant) selected from among ammonium sulphate or polyethylene-glycols (PEG) having a molecular weight (MW) not lower than 4,000, and at an end concentration such as to make it possible the above said complexes to precipitate quantitatively.

Preferably, PEG-6000 is used, at an end concentration comprised within the range of from 13% to 17% (W/V).

In this step, the process is carried out with the mixtures being kept mildly stirred, at temperatures comprised within the range of from 15° C. to 35° C., preferably of from 20° to 30° C., for a time of from 40 to 60 minutes.

By operating under said preferred conditions, PEG-6000 precipitates all the immunoglobulins present in the sample, including the Ab-P and Ab-P-E complexes, leaving in solution the unreacted antigens.

The (c) Step

In this step, the precipitate is separated from the reaction mixtures by centrifugation or filtration.

The separation of the precipitate is preferably carried out by filtration, in that, by operating with small volumes (of the order of microliters), the steps of the same process are simpler.

For that purpose, filtering equipment can be used, which are available from the market, such as, e.g., the Millititer Filtration System by Millipore Corp. Said system consists of filtering plates with a size of the pores of 0.22 μm which, once used, can, differently from the absorbent plates used in the ELISA test, be washed and used again for successive analyses.

The (d) Step

In this step, the precipitate present on the filtering plates is repeatedly washed (generally, 3-4 times), with the PBS/D buffer solution containing the precipitating substance at an end concentration comprised within the range of from 13% to 17%.

The (e) Step

According to the present invention, in this step the precipitate is dissolved by means of the addition, all at once, or as successive aliquots, of a 0.1M acetate or acetate-citrate buffer solution at a pH value of from 4 to 5.5, containing a non-ionic and/or a weak anionic detergent at the same concentrations as reported in the (a) step, in the presence, or not, of the precipitating solution at an end concentration comprised within the range of from 3% to 5% (W/V).

Preferably, a buffer solution at a pH value of, or approximately of, 5.0 is used, which contains PEG-6000 at 4% and 0.05% Triton X-100.

The presence of the detergent as the dispersant proved to be particularly advantageous in the stabilization and recovery of the antibody-antigen-enzyme complex. The precipitating substance at the above reported concentrations performs, on the contrary, the function of lowering the aspecific background of the end enzymatic answer.

In fact, said substance, at the above reported pH values, renders insoluble most precipitated matters of non-immunoglobulinic nature having peroxidasic activity.

The (f) Step

In accordance with the process of the instant invention, this step is carried out by adding to the mixtures obtained in the (e) step a colourless substrate specific for the used enzyme.

Preferably, when the enzyme is peroxidase (E.C. 1. 11. 1.7), the specific substrate is ABTS [2,2-azino-di-(3-benzothiazoline-sulphonate)] or TMB (3,3',5,5'-tetramethyl-benzidine).

The colorimetric reaction is carried out, in the presence of hydrogen peroxide, at a temperature comprised within the range of from 15° to 35° C., preferably of from 20° to 30° C., and for a suitable time period.

Generally, a time of from 10 to 30 minutes is enough. According to the method of the present invention, TMB and $H_2O_2$ at end concentrations of respectively 0.1 mg/ml and 1.3 mM are preferably used, and the required reaction time under these conditions is of 10 minutes. At the end, the enzymatic reaction is stopped by means of the addition of a strong acid, such as, e.g., $H_2SO_1$ at a concentration comprised within the range of from 2 to 3 molar. For each aliquot, the colour intensity is then evaluated by determining the absorbance by means of a spectrophotometric reading vs. a blank—i.e., a substrate prepared as disclosed in the various steps of the present invention, in the absence of a blood sample.

The specific value, or specific absorbance (A) relevant to the Ab-P-E complex for each sample is given by:

$$A(sample+P-E)-A[sample+(P+P-E)],$$

i.e., from the difference between the total absorbance (specific absorbance+aspecific absorbance) and the aspecific absorbance.

According to the present invention, the criterion used in order to classify the samples as "positive" or "negative" is the following:
- a sample is regarded as "positive" when its specific (A) ["A(spec.)"] is higher than 0.100 and represents at least 30% of total A (total specific and aspecific absorbance);
- a sample is regarded as "negative" when its A(spec.) is lower than 0.100, whichever the value of % inhibition is.

In accordance with the present invention, the sensitivity of the method is such as to make it possible to detect antisporozoite-antibodies at a concentration equal to, or approximately equal to, 0.2 ng/μl of serum.

Furthermore it was found that the results obtained by operating in accordance with the method of the present invention at a temperature of 30° C. are identical to those observed at temperatures of 20°-25° C. This fact makes it possible said method to be advantageously used in tropical areas, in which malaria is more diffused.

Summing up, the method according to the present invention shows considerable advantages as compared to the present state of the art, and, in particular, over the ELISA method.

Among them, the high sensitivity and reproducibility of the results, the rapidity and precision of execution, as well as the cheapness of the same method have to be mentioned.

The sensitivity of the method according to the present invention is to be attributed to the fact that the reaction of formation of the complex between the antisporozoite antibodies and the synthetic antigen, and of the end colorimetric development take place in homogeneous phase, and under determined conditions.

Furthermore, the method according to the present invention, by being based on the inhibition of the specific value of each sample with the pure (unlabeled) antigen, supplies a specific immunodiagnostic, semquantitative response, amplified by the greater sensitivity of the same method.

As regards the cheapness of the method of the present invention, it requires, besides the synthetic antigen and the necessary reactants for the execution of the test, available from the market, the P-E conjugate, which is endowed with the advantage of being cheaper than the antibody-antihuman conjugate.

A considerable advantage of the process according to the present invention consists also in the possibility of a simple execution.

Furthermore, the method, due to its versatility, by being suitable for testing both small and large sample numbers, is also suitable for use in sanitary units with low-volume diagnostic demands. For the determination of the anti-*P. falciparum*-sporozoite antibodies on samples of human blood, analytical packages are well suitable, which contain all the necessary reactants for carrying out the method according to the present invention, like, e.g., a kit consisting of a synthetic antigen, a synthetic antigen-enzyme conjugate, a substrate, buffer solutions and a substance capable of precipitating the antigen-antibody complex.

An analytical package of this type, or of a similar type, makes it possible anti-Plasmodium-sporozoite antibodies to be determined with a cost as low as possible.

The following experimental examples are illustrative and non-limitative of the same invention.

Example 6 is a comparison with the conventional ELISA methods.

EXAMPLE 1

Sixteen sera were used, which were given the reference codes 241-711 and KX, of unknown origin, drawn from healthy individuals and from malariated individuals, a serum and a heparinic plasma drawn from two healthy donors, a serum from a healthy donor made positive by means of the addition of two monoclonal (Mab) anti-(NANP)$_3$ antibodies (1 and 2 ng/$\mu$l of whole serum).

The samples were diluted 1:50 inside Eppendorf test tubes with the PBS/D buffer solution at pH value=7.5 (PBS=0.01M sodium phosphate, 0.3M NaCl, D=0.05% Triton X-100, V/V and 0.05% sodium-lauroyl sarcosine, (W/V).

In practice, 5 $\mu$l of serum, plasma and Mab/negative serum were diluted with 245 $\mu$l of PBS/D.

Four aliquots (50 $\mu$l) of each sample, so diluted, were then charged to a series of four adjacent wells belonging to a vertical row of a 96-wells plate. Therefore, a plate results to be complete with 22 samples, with the first row being reserved to the blank, i.e., to the only substrate of the end enzymatic reaction.

To the third and to the fourth wells relevant to each sample, 2 $\mu$l were added of a solution of the synthetic peptide (NANP)$_{20}$ (P) in distilled water (1 $\mu$g/$\mu$l).

Subsequently, to all the wells with the samples, 50 $\mu$l were added of a solution of the P-E conjugate in PBS/D (2 $\mu$g/ml).

After 20 minutes at room temperature (20°-25° C.), into the single wells 0.1 ml was introduced of a 30% solution of PEG-6000 (Fluka) (W/V) in PBS/D.

Owing to the high density of this solution, a good mixing with the sample was obtained by placing inside each well a small steel ball of 3.1 mm of diameter, with the plate being then slightly rotated.

The plates were maintained at room temperature for 60 minutes, and from each well 0.1 ml of sample was then drawn and transferred into the corresponding wells of a filtering plate (Millipore, STGV 096 NS 0.22 $\mu$m).

The samples were filtered with suction and were then washed four times, each time with 0.2 ml of PEG-6000 at 15% in PBS/D.

The precipitates on the filter were then dissolved by introducing into each well 0.150 ml of 0.1M acetate buffer solution at pH 5.0 containing Triton X-100 (0.05% and PEG-6000 (4%) (the "a" solution). The plate was maintained 5 minutes, with mild shaking, at room temperature.

The solutions were then collected, by suction, into the underlying receiving plate.

The suction was then repeated with 0.1 ml of the same "a" solution.

The receiving plate was then recovered, and to each well 30 $\mu$l was added of a solution containing 3,3',5,5'-tetramethyl-benzidine (TMB) and H$_2$O$_2$ at an end concentration of respectively 0.1 mg/ml and 1.3 mM.

The enzymatic reaction was stopped by adding to each well, after 10 minutes, 25 $\mu$l of 3M H$_2$SO$_4$. The absorbance of the solutions of each well was then measured at 450 nm with a plate reader Titertek Multiskan Plus.

The results obtained are reported in Table 1:

TABLE 1

A at 450 nm after 10 Minutes, Reaction with TMB

| Sample (0.5 $\mu$l) | P-E (a) | P-E + P (b) | A (spec.) (a − b) | Inhibition % (spec. %) $\left(100 \times \frac{a-b}{a}\right)$ |
|---|---|---|---|---|
| Negative serum + Mab (0.5 ng) | 0.438 | 0.073 | 0.365 | 100 |
| Negative serum + Mab (1.0 ng) | 0.694 | 0.063 | 0.631 | 100 |
| Negative serum | 0.058 | 0.056 | — | — |
| Negative plasma | 0.105 | 0.102 | — | — |
| 241 | 1.572 | 0.644 | 0.928 | 59 |
| 273 | 2.356 | 0.479 | 1.877 | 80 |

TABLE 1-continued

A at 450 nm after 10 Minutes, Reaction with TMB

| Sample (0.5 µl) | P-E (a) | P-E + P (b) | A (spec.) (a − b) | Inhibition % (spec. %) $\left(100 \times \frac{a-b}{a}\right)$ |
|---|---|---|---|---|
| 575 | 1.600 | 1.031 | 0.569 | 36 |
| 578 | 1.742 | 0.482 | 1.260 | 72 |
| 615 | 0.116 | 0.123 | — | — |
| 620 | 2.040 | 1.029 | 1.011 | 50 |
| 632 | 0.986 | 0.516 | 0.470 | 48 |
| 644 | 2.336 | 0.605 | 1.731 | 74 |
| 664 | 0.129 | 0.098 | — | — |
| 672 | 0.128 | 0.103 | — | — |
| 681 | 2.317 | .578 | 1.739 | 75 |
| 690 | 2.452 | 1.726 | 0.726 | 30 |
| 705 | 0.170 | 0.177 | — | — |
| 709 | 0.102 | 0.098 | — | — |
| 711 | 1.982 | 0.381 | 1.601 | 81 |
| KX | 1.476 | 0.733 | 0.743 | 50 |

In the Table:
(a) is the specific absorbance + the non-specific absorbance;
(b) is the non-specific absorbance;
A (spec.) is the specific absorbance;
Inhibition % or specificity % indicates the specificity of the method.

EXAMPLE 2

The process was carried out as reported in the preceding Example 1, by using:
- a solvent for the precipitate, constituted by 0.1M acetate buffer solution at pH 5.0, containing 0.05% Triton X-100 (the "b" solution), and
- a solution (30 µl/well) containing 2,2'-azino-di-(3-ethyl-benzothiazoline)-sulphonate (ABTS) and $H_2O_2$ at an end concentration respectively of 1.1 mg/ml, and 1.3 mM.

The absorbances were measured for each well at 405 nm, without stopping the enzymatic reaction, after 15 and 30 minutes.

In Tables 2 and 3, the results are reported, which were respectively obtained with a reaction time of 15 minutes and of 30 minutes.

TABLE 2

A at 405 nm after 15 Minutes of Reaction (ABTS)

| Sample (0.5 µl) | P-E (a) | P-E + P (b) | A (spec.) (a − b) | Inhibition % $\left(100 \times \frac{a-b}{a}\right)$ |
|---|---|---|---|---|
| Negative serum + Mab (0.5 ng) | 0.308 | 0.105 | 0.203 | 100 |
| Negative serum + Mab (1.0 ng) | 0.525 | 0.128 | 0.397 | 100 |
| Negative serum | 0.120 | 0.106 | — | — |
| Negative plasma | 0.137 | 0.122 | — | — |
| 241 | 0.730 | 0.443 | 0.287 | 39 |
| 273 | 1.444 | 0.320 | 1.124 | 79 |
| 575 | 0.752 | 0.490 | 0.262 | 35 |
| 578 | 0.670 | 0.319 | 0.351 | 52 |
| 615 | 0.142 | 0.153 | — | — |
| 620 | 0.789 | 0.440 | 0.349 | 44 |
| 632 | 0.540 | 0.346 | 0.194 | 36 |
| 644 | 0.999 | 0.342 | 0.657 | 66 |
| 664 | 0.083 | 0.080 | — | — |
| 672 | 0.163 | 0.135 | — | — |
| 681 | 0.955 | 0.423 | 0.532 | 56 |
| 690 | 1.924 | 0.823 | 1.101 | 57 |
| 705 | 0.232 | 0.201 | — | — |
| 709 | 0.120 | 0.117 | — | — |
| 711 | 0.801 | 0.306 | 0.495 | 62 |
| KX | 0.635 | 0.385 | 0.250 | 39 |

TABLE 3

A at 405 nm after 30 Minutes of reaction (ABTS)

| Sample (0.5 µl) | P-E (a) | P-E + P (b) | A (spec.) (a − b) | Inhibition % $\left(100 \times \frac{a-b}{a}\right)$ |
|---|---|---|---|---|
| Negative serum + Mab (0.5 ng) | 0.603 | 0.203 | 0.400 | 100 |
| Negative serum + Mab (1.0 ng) | 1.006 | 0.248 | 0.758 | 100 |
| Negative serum | 0.240 | 0.218 | — | — |
| Negative plasma | 0.270 | 0.242 | — | — |
| 241 | 1.372 | 0.863 | 0.509 | 37 |
| 273 | 2.195 | 0.614 | 1.581 | 72 |
| 575 | 1.412 | 0.954 | 0.458 | 32 |
| 578 | 1.264 | 0.612 | 0.652 | 52 |
| 615 | 0.285 | 0.292 | — | — |
| 620 | 1.481 | 0.853 | 0.628 | 42 |
| 632 | 1.045 | 0.684 | 0.361 | 35 |
| 644 | 1.806 | 0.669 | 1.137 | 63 |
| 664 | 0.170 | 0.173 | — | — |
| 672 | 0.317 | 0.271 | — | — |
| 681 | 1.773 | 0.835 | 0.938 | 53 |
| 690 | 2.311 | 1.545 | 0.976 | 42 |
| 705 | 0.464 | 0.406 | — | — |
| 709 | 0.242 | 0.234 | — | — |
| 711 | 1.518 | 0.610 | 0.908 | 60 |
| KX | 1.228 | 0.763 | 0.465 | 38 |

EXAMPLE 3

The analytical method was carried out by operating as reported in the preceding Example 1, using the (a) solution as the solvent for the precipitate; ABTS as the enzymatic substrate; and a reaction time of 30 minutes.

In following Table 4, the results obtained are reported:

TABLE 4

A at 405 nm after 30 Minutes of reaction (ABTS)

| Sample (0.5 µl) | P-E (a) | P-E + P (b) | A (spec.) (a − b) | Inhibition % $\left(100 \times \frac{a-b}{a}\right)$ |
|---|---|---|---|---|
| Negative serum + Mab (0.5 ng) | 0.231 | 0.031 | 0.200 | 100 |
| Negative serum + Mab (1.0 ng) | 0.352 | 0.035 | 0.37 | 100 |
| Negative serum | 0.038 | 0.036 | — | — |
| Negative plasma | 0.050 | 0.036 | — | — |
| 241 | 0.770 | 0.243 | 0.527 | 68 |
| 273 | 1.584 | 0.224 | 1.360 | 86 |
| 575 | 0.624 | 0.345 | 0.279 | 45 |

TABLE 4-continued

A at 405 nm after 30 Minutes of reaction (ABTS)

| Sample (0.5 μl) | P-E (a) | P-E + P (b) | A (spec.) (a − b) | Inhibition % $\left(100 \times \frac{a-b}{a}\right)$ |
|---|---|---|---|---|
| 578 | 0.615 | 0.213 | 0.402 | 65 |
| 615 | 0.058 | 0.045 | — | — |
| 620 | 0.763 | 0.360 | 0.403 | 53 |
| 632 | 0.444 | 0.219 | 0.225 | 51 |
| 644 | 1.316 | 0.244 | 1.072 | 81 |
| 664 | 0.056 | 0.042 | — | — |
| 672 | 0.059 | 0.046 | — | — |
| 681 | 1.168 | 0.315 | 0.853 | 73 |
| 690 | 2.218 | 0.718 | 1.500 | 68 |
| 705 | 0.095 | 0.072 | — | — |
| 709 | 0.044 | 0.042 | — | — |
| 711 | 0.897 | 0.198 | 0.699 | 78 |
| KX | 0.630 | 0.310 | 0.320 | 51 |

EXAMPLE 4

The process was carried out in the same way as disclosed in Example 2, on a sample of positive serum (KX), using the ABTS substrate, a reaction time of 30 minutes, and a PBS/D buffer solution containing different (D) detergents at different concentrations.

The results are reported in following Table 5.

The absorbance was determined at 405 nm, using 0.5 μl of sample.

TABLE 5

A at 405 nm after 30 Minutes with ABTS

| Detergent (D) | P − E | P − E + P | A (spec.) | Inhibition % |
|---|---|---|---|---|
| Tween 20 (0.05%) | 0.989 | 0.590 | 0.399 | 40 |
| Tween 20 (0.2%) | 0.917 | 0.504 | 0.413 | 45 |
| Triton X-100 (0.05%) | 0.758 | 0.335 | 0.423 | 56 |
| Triton X-100 (0.01%) | 0.838 | 0.340 | 0.498 | 59 |
| Triton X-100 (0.2%) | 0.759 | 0.406 | 0.353 | 46 |
| Saponine (0.05%) | 0.741 | 0.310 | 0.431 | 58 |
| Na-L Sarc. (0.05%) | 0.630 | 0.284 | 0.346 | 55 |
| Na-C (0.086%) | 0.876 | 0.438 | 0.438 | 50 |
| Na + DOC (0.086%) | 1.005 | 0.576 | 0.429 | 43 |
| Triton X-200 (0.05%) | 0.686 | 0.206 | 0.480 | 70 |
| Na-L Sar C. (0.05%) | | | | |

EXAMPLE 5

The process was carried out by operating with the positive serum KX as reported in the preceding Example 2, using, for dissolving the precipitate in the (e) step buffer solutions at different pH values and concentrations of PEG-6000.

The results are reported in following Table 6:

TABLE 6

A at 405 nm after 20 Minutes with ABTS

| pH | PEG-6000 % | P − E | P − E + P | A (spec.) | Inhibition % |
|---|---|---|---|---|---|
| 4.5 | 3 | 0.506 | 0.180 | 0.326 | 64 |
| 4.5 | 4 | 0.416 | 0.155 | 0.261 | 63 |
| 4.5 | 5 | 0.320 | 0.140 | 0.180 | 56 |
| 5.0 | 3 | 0.492 | 0.192 | 0.300 | 61 |
| 5.0 | 4 | 0.362 | 0.116 | 0.246 | 68 |
| 5.0 | 5 | 0.246 | 0.063 | 0.183 | 74 |
| 5.5 | 3 | 0.318 | 0.103 | 0.215 | 67 |
| 5.5 | 4 | 0.198 | 0.044 | 0.154 | 77 |
| 5.5 | 5 | 0.131 | 0.021 | 0.110 | 84 |

EXAMPLE 6

Comparison With Known Methods a) "ELISA" Test

In this test, there were used 0.5 μl of the same samples as reported in Example 1, and two plates pretreated as follows:
- one plate, with 0.1 μg/well of a synthetic antigen (NANP) and then with BSA (bovine seroalbumin) at 3%-PBS;
- the other one, with BSA alone.

To each well of both plates, the antihuman-antibody-alkaline phosphatase conjugate (Ab''-PA) was then added, which, with the antisporozoite antibody (Ab) possibly present in the sample forms the P-Ab-Ab''-PA complex.

The detection was carried out, by operating according to known techniques, by using the paranitrophenyl-phosphate (p-NPP) substrate.

The enzymatic reaction was stopped after 30 minutes by means of the addition of 25 μl of 3M NaOH.

The absorbance was measured at 405 nm.

The specific value [A (spec)] is given by: Absorbance(plate with $(NANP)_{40}$) - Absorbance(plate with BSA).

The results are reported in following Table 7.

TABLE 7

A at 405 nm after 30 Minutes with p-NPP

| Sample (0.5 μl of serum) | $(NANP)_{40}$ (a) | BSA (b) | A (spec.) (a − b) | Specificity % $\left(100 \times \frac{a-b}{a}\right)$ |
|---|---|---|---|---|
| Positive serum + Mab low | 0.398 | 0.191 | 0.207 | 52 |
| Positive serum + Mab high | 0.873 | 0.060 | 0.813 | 93 |
| Negative serum | 0.012 | 0.020 | — | — |
| Negative plasma | 0.027 | 0.043 | — | 72 |
| 241 | 0.605 | 0.172 | 0.433 | 97 |
| 273 | 0.737 | 0.024 | 0.713 | 65 |
| 575 | 0.234 | 0.082 | 0.152 | 76 |
| 578 | 0.328 | 0.078 | 0.250 | — |
| 615 | 0.006 | 0.032 | — | — |
| 620 | 0.195 | 0.055 | 0.140 | 72 |
| 632 | 0.111 | 0.126 | — | — |
| 644 | 0.520 | 0.048 | 0.472 | 91 |
| 664 | 0.005 | 0.020 | — | — |
| 672 | 0.008 | 0.049 | — | — |
| 681 | 0.338 | 0.110 | 0.228 | 67 |
| 690 | 2.249 | 0.079 | 2.170 | 96 |
| 705 | 0.008 | 0.023 | — | — |
| 709 | 0.005 | 0.036 | — | — |
| 711 | 0.368 | 0.085 | 0.283 | 77 |
| KX | 0.152 | 0.035 | 0.117 | 77 |

B) P-E/Sepharose-A-Protein (P.E/S-PA) Method

The method, disclosed in co-pending U.S. patent application No. 134,229, now Patent No. 4,977,079, is characterized in that it operates with the synthetic antigen-enzyme conjugate (P-E), which is capable of forming with the antisporozoite antibodies present in the sample of blood, a stable antibody-synthetic antigen-enzyme complex (Ab-P-E), which is bonded to A Protein.

In practice, the samples to be analysed were prepared as reported in the preceding Example 1, using the PBS/Triton X-100 0.05% buffer solution. After 20 minutes of reaction, the samples were transferred into the wells of a filtering plate (Millipore) containing the Sepharose-A Protein resin (2 mg of commercial freeze-dried product/well) (Pharmacia-Uppsala) equilibrated with the same buffer solution.

The plate was incubated at room temperature for 30 minutes, and was then washed 4 times with the same equilibration buffer solution.

To each well, 150 μl was then charged of 0.1M acetate buffer, pH 5.0, containing the ABTS substrate and $H_2O_2$ at the end concentration, respectively, of 1.1 mg/ml and 1.3 mM.

Thirty minutes later, the positivity, or negativity, of the samples, was determined by observing the reaction colour in the individual wells.

The positive sera (malariated sera), and the Mab-containing sera showed a green-blue colour in the wells relevant to the reaction mixture serum+P-E, and no colour, or a slight colour only, in the wells which contained the serum+P−E+P mixture; the negative sera were colourless, or slightly coloured in a same way in the wells relevant to the two reactions.

In following Table 8, the values are reported, which were obtained for the 16 sera with the method according to the present invention P-E/PEG (1), with the ELISA method (2), and with the P-E-/S-PA method (3): besides the values of specific A [A(spec.)], the positivity (+) and the negativity (−) are displayed.

TABLE 8

Comparison between the specific absorbances obtained by means of the method according to the present invention (1) and the methods known from the prior art (2) and (3)

| Samples | Method 1 P − E/PEG | | | Method 2 ELISA | Method 3 P − E/S − PA |
|---|---|---|---|---|---|
| | A (spec.) from Table 3 | A (spec.) from Table 4 | A (spec.) from Table 1 | A (spec.) from Table 7 | |
| 241 | 0.509 (+) | 0.527 (+) | 0.928 (+) | 0.433 (+) | + |
| 273 | 1.581 (+) | 1.360 (+) | 1.877 (+) | 0.713 (+) | + |
| 575 | 0.458 (+) | 0.279 (+) | 0.569 (+) | 0.152 (+) | + |
| 578 | 0.652 (+) | 0.402 (+) | 1.260 (+) | 0.250 (+) | + |
| 615 | (−) | (−) | (−) | (−) | − |
| 620 | 0.628 (+) | 0.403 (+) | 1.011 (+) | 0.140 (+) | + |
| 632 | 0.361 (+) | 0.225 (+) | 0.470 (+) | (−) | + |
| 644 | 1.137 (+) | 1.012 (+) | 1.731 (+) | 0.472 (+) | + |
| 664 | (−) | (−) | (−) | (−) | − |
| 672 | (−) | (−) | (−) | (−) | − |
| 681 | 0.938 (+) | 0.853 (+) | 1.739 (+) | 0.228 (+) | + |
| 690 | 0.976 (+) | 1.500 (+) | 0.726 (+) | 2.170 (+) | + |
| 705 | (−) | (−) | (−) | (−) | − |
| 709 | (−) | (−) | (−) | (−) | − |
| 711 | 0.908 (+) | 0.699 (+) | 1.601 (+) | 0.283 (+) | + |
| KX | 0.465 (+) | 0.320 (+) | 0.743 (+) | 0.117 (+) | + |

From a comparison of the test results reported in Table 8, one can observe that:

1. for one only of the 16 unknown sera tested, namely, serum No. 632, a conflict exists, in that this serum results to be negative according to the ELISA test, and positive when tested according to the other two methods;
2. in case of positive sera, the P-E/PEG method gives, with both the ABTS and the TMB substrate, values of A(spec.) higher than ELISA, and is therefore capable of detecting the positivity of serum No. 632;
3. the low values of A(spec) in ELISA for sera Nos. 570, 620 and KX, should a cut-off of 0.150 be used, would cause these three sera to be classified as uncertain ("borderline"), whilst they result surely positive according to the other two methods.

We claim:

1. Immuno-enzymatic method for the determination of anti-*P. falciparum*-sporozoite antibodies in a sample of blood, which comprises:

(a) separately incubating two aliquots, (i) and (ii), of a same sample with a synthetic antigen-enzyme conjugate (P-E), wherein the synthetic antigen (P) of the conjugate is capable of reacting with anti-*P. falciparum*-sporozoite antibodies present in the sample to form an antisporozoite-synthetic antigen-enzyme complex and the enzyme (E) of the conjugate is capable of catalyzing a colormetric reaction, in phosphate buffer at a pH value within the range of from 6.5 to 8.00, in the presence of a non-ionic and/or weak anoinic detergent at a concentration now lower than 0.05% (weight/volume or volume/volume) (w/w or v/v), and at a temperature within the range of from 15° C. to 35° C., wherein one aliquot (i) of the sample has been previously admixed with the same synthetic antigen (P) not labeled with the enzyme at such a concentration as to completely inhibit the formation of the antisporozoite antibody-synthetic antigen-enzyme complex (Ab-P-E);

(b) adding to the samples treated as reported in step (a), PEG 6000 as an inert substance capable of quantitatively precipitating the antisporozoite antibody-synthetic antigen-enzyme complex at an end concentration within the range of 13% to 17% (W/V);

(c) separating precipitate from the reaction mixtures obtained in step (b), either by filtration by centrifugation;

(d) repeatedly washing precipitate obtained in step (c) with a buffer solution to which the PEC 6000 is added, up to an end concentration within the range of from 13% to 17% (W/V);

(e) dissolving the so obtained precipitate in a buffer solution at a small pH value within the range of from 4.0 to 5.5, containing a non-ionic and/or weak anionic detergent at an end concentration not lower than 0.05% (w/v or v-v), in the presence or not of the PEG 6000, at an end concentration within the range of from 3% to 5% (w/v);

(f) adding to the so obtained solutions, a colorless enzymatic substrate, specific for the enzyme used and capable of generating, at a pH within the range of 4.0 to 5.5, in case the sample under examination is positive, a colored product; and (g) finally determining the intensity of the color by comparative absorbance spectrophotometry between aliquot (i) and aliquot (ii).

2. Immunoenzymatic method according to claim 1, wherein in step (a) the sample of human blood to be analysed is whole blood, serum or plasma.

3. Immunoenzymatic method according to claim 1, wherein in step (a) the synthetic antigen is defined by the amnioacidic sequence (Asn-Ala-Asn-Pro)$_n$, wherein:

Asn=asparagine,
Ala=alanine, and
Pro=proline, and wherein n' has a value within the range from 3 to 40.

4. Immunoenzymatic method according to claim 1, wherein in step (a) the enzyme is peroxidase or acidic phosphatase.

5. Immunoenzymatic method according to claim 1, wherein in step (a) the non-ionic detergent is Tween-20, Triton X-100, or Saponine, and the weak anionic detergent is sodium chlorate, sodium deoxychlorate, or sodium lauroyl-sarcosinite.

6. Immunoenzymatic method according to claim 1, wherein in step (a) process is carried out as a temperature within the range of from 50° to 35° C., for a corresponding time period of from 30 minutes to 1.5 hours.

7. Immunoenzymatic method according to claim 6 wherein in step (a) the temperature is within the range of from 2° to 3° C. and the reaction time is equal to, or approximately equal to, 60 minutes.

8. Immunoenzymatic method according to claim 1, wherein in step (a) the buffer solution has a pH of 5.0, and the PEG 6000 is at a concentration of 4% (W/V).

9. Immunoenzymatic method according to claim 1, wherein in step (a) the enzyme is peroxidase, and the substrate is 2,2'-azino-di-(3-ethyl-benzothiazoline-sulphonate) (ABTS) or 3,3',5,5'-tetramethyl-benzidine (TMB).

10. Diagnostic kit for detecting the anti-*P. falciparum*-sporozoite antibodies in a sample of human blood, which comprises the necessary reactants for carrying out the method according to claim 1, including a synthetic antigen, a synthetic antigen-enzyme conjugate, a substrate, suitable buffer solutions and PEG 6000.

* * * * *

UNITED STATES PATENT AND TRADEMARK OFFICE
CERTIFICATE OF CORRECTION

PATENT NO. : 5,210,018
DATED : May 11, 1993
INVENTOR(S) : Carlo A. Nuzzolo et al.

It is certified that error appears in the above-identified patent and that said Letters Patent is hereby corrected as shown below:

COLUMN 14:

In Claim 1, in line 16, "w/w" should read as --w/v--;

In Claim 1, in line 34, "PEC" should read as --PEG--;

In Claim 3, in line 3, "amnioacidic" should read as --aminoacid--; and

In Claim 6, in line 3, "50 " should read as --15 --.

Signed and Sealed this

First Day of February, 1994

Attest:

BRUCE LEHMAN

Attesting Officer

Commissioner of Patents and Trademarks